(12) United States Patent
Park et al.

(10) Patent No.: US 8,778,901 B2
(45) Date of Patent: Jul. 15, 2014

(54) ANTICANCER DRUG COMPRISING INHIBITOR OF TMPRSS4

(75) Inventors: Young Woo Park, Daejon (KR); Semi Kim, Daejon (KR); Kiwon Jo, Daejon (KR); Ji Hyun Park, Gyeonsangnam-do (KR); Heekyung Jung, Daejon (KR); Kwang Pyo Lee, Seoul (KR); So Jeong Park, Daejon (KR); Young-soon Jang, Daejon (KR); So-Young Choi, Daejon (KR); Joon-Goo Jung, Incheon (KR); Hyo Jeong Hong, Gongju-si (KR); Jeong Ho Yoon, Seoul (KR); Jong-Ho Park, Seoul (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 1158 days.

(21) Appl. No.: 12/227,923

(22) PCT Filed: Nov. 10, 2006

(86) PCT No.: PCT/KR2006/004702
§ 371 (c)(1),
(2), (4) Date: Dec. 1, 2008

(87) PCT Pub. No.: WO2007/139260
PCT Pub. Date: Dec. 6, 2007

(65) Prior Publication Data
US 2011/0318361 A1 Dec. 29, 2011

(30) Foreign Application Priority Data
May 30, 2006 (KR) .................. 10-2006-0048685

(51) Int. Cl.
*A61K 48/00* (2006.01)

(52) U.S. Cl.
USPC .......................................... 514/44; 536/24.5

(58) Field of Classification Search
None
See application file for complete search history.

(56) References Cited

U.S. PATENT DOCUMENTS 7,842,291 B1 * 11/2010 Ruben et al. ............... 424/130.1
2003/0143732 A1 * 7/2003 Fosnaugh et al. ............ 435/325

FOREIGN PATENT DOCUMENTS

WO  WO 02/092841 A   11/2002
WO  2004097034 A2    11/2004

OTHER PUBLICATIONS

Wallrapp et al., "A Novel Transmembrane Serine Protease (TMPRSS3) Overexpressed in Pancreatic Cancer." Cancer Res., 60:2602-2606, May 15, 2000.
El Kebebew, et al., ECM1 and TMPRSS4 Are Diagnostic Markers of Malignant Thyroid Neoplasms and Improve the Accuracy of Fine Needle Aspiration Biopsy, Annals of Surgery 2005: 242: 353-363 (Sep. 2005).

* cited by examiner

*Primary Examiner* — Kimberly Chong
(74) *Attorney, Agent, or Firm* — Lucas & Mercanti, LLP

(57) ABSTRACT

The present invention relates to an anticancer agent containing a TMPRSS4 (transmembrane protease, serine 4) inhibitor as an effective ingredient, more precisely an anticancer agent containing an inhibitor of TMPRSS4 activity as an effective ingredient. The anticancer agent of the present invention can be used effectively for the treatment of cancer by inhibiting TMPRSS4 expression in cancer cells and thereby inhibiting cancer cell invasion and cancer cell growth.

3 Claims, 11 Drawing Sheets

FIG. 4
No transfection
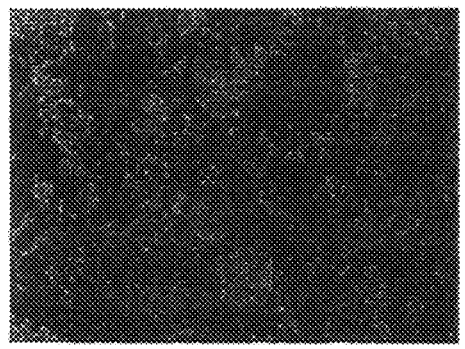
Negative control siRNA
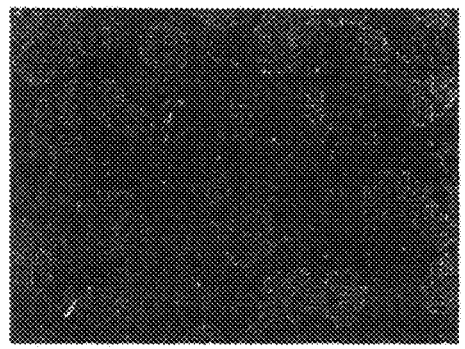
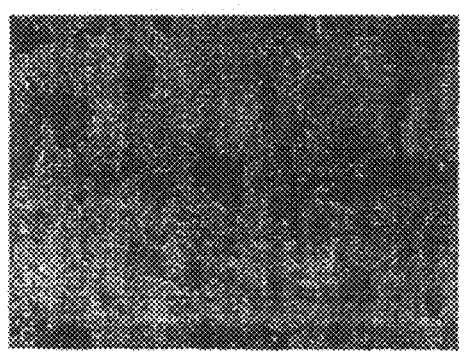
siRNA-TMPRSS4-01
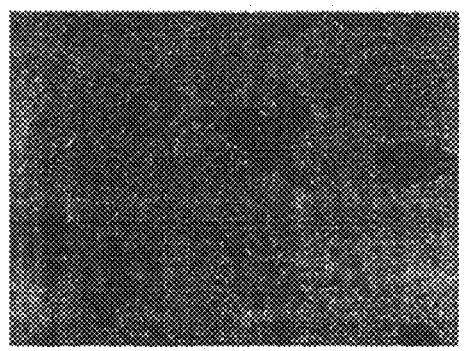
siRNA-TMPRSS4-02

```
                           SEQUENCE LISTING

<160> NUMBER OF SEQ ID NOS: 22

<210> SEQ ID NO 1
<211> LENGTH: 21
<212> TYPE: DNA
<213> ORGANISM: Artificial Sequence
<220> FEATURE:
<223> OTHER INFORMATION: TMPRSS4 fragment sense primer

<400> SEQUENCE: 1
tacaatgtct ggaaggctga g                                             21

<210> SEQ ID NO 2
<211> LENGTH: 21
<212> TYPE: DNA
<213> ORGANISM: Artificial Sequence
<220> FEATURE:
<223> OTHER INFORMATION: TMPRSS4 fragment antisense primer

<400> SEQUENCE: 2
ttcttgctct agtaggcttg g                                             21

<210> SEQ ID NO 3
<211> LENGTH: 20
<212> TYPE: DNA
<213> ORGANISM: Artificial Sequence
<220> FEATURE:
<223> OTHER INFORMATION: TMPRSS4 sense primer

<400> SEQUENCE: 3
ccgatgtgtt caactggaag                                               20

<210> SEQ ID NO 4
<211> LENGTH: 20
<212> TYPE: DNA
<213> ORGANISM: Artificial Sequence
<220> FEATURE:
<223> OTHER INFORMATION: TMPRSS4 antisense primer

<400> SEQUENCE: 4
cccatccaat gatccagagt                                               20

<210> SEQ ID NO 5
<211> LENGTH: 25
<212> TYPE: DNA
<213> ORGANISM: Artificial Sequence
<220> FEATURE:
<223> OTHER INFORMATION: GAPDH sense primer

<400> SEQUENCE: 5
tgatgacatc aagaaggtgg tgaag                                         25

<210> SEQ ID NO 6
<211> LENGTH: 23
<212> TYPE: DNA
```

-continued

```
<213> ORGANISM: Artificial Sequence
<220> FEATURE:
<223> OTHER INFORMATION: GAPDH antisense primer

<400> SEQUENCE: 6
tccttggagg ccatgtgggc cat                                        23

<210> SEQ ID NO 7
<211> LENGTH: 25
<212> TYPE: RNA
<213> ORGANISM: Artificial Sequence
<220> FEATURE:
<223> OTHER INFORMATION: siRNA-TMPRSS4-01 sense sequence

<400> SEQUENCE: 7
aaguugucga acaggcaga gaacc                                       25

<210> SEQ ID NO 8
<211> LENGTH: 25
<212> TYPE: RNA
<213> ORGANISM: Artificial Sequence
<220> FEATURE:
<223> OTHER INFORMATION: siRNA-TMPRSS4-01 antisense primer

<400> SEQUENCE: 8
gguucucugc cguuucgac aacuu                                       25

<210> SEQ ID NO 9
<211> LENGTH: 25
<212> TYPE: RNA
<213> ORGANISM: Artificial Sequence
<220> FEATURE:
<223> OTHER INFORMATION: siRNA-TMPRSS4-02 sense sequence

<400> SEQUENCE: 9
cagacgugcu guuugucgua cugga                                      25

<210> SEQ ID NO 10
<211> LENGTH: 25
<212> TYPE: RNA
<213> ORGANISM: Artificial Sequence
<220> FEATURE:
<223> OTHER INFORMATION: siRNA-TMPRSS4-02 antisense sequence

<400> SEQUENCE: 10
uccaguacga caaacagcac gucug                                      25

<210> SEQ ID NO 11
<211> LENGTH: 25
<212> TYPE: RNA
<213> ORGANISM: Artificial Sequence
<220> FEATURE:
<223> OTHER INFORMATION: siRNA-TMPRSS4-03 sense sequence

<400> SEQUENCE: 11
uauguuuccu gaagcagugg gcugc                                      25

<210> SEQ ID NO 12
<211> LENGTH: 25
<212> TYPE: RNA
<213> ORGANISM: Artificial Sequence
<220> FEATURE:
<223> OTHER INFORMATION: siRNA-TMPRSS4-03 antisense sequence

<400> SEQUENCE: 12
gcagcccacu gcuucaggaa acaua                                      25
```

```
<210> SEQ ID NO 13
<211> LENGTH: 31
<212> TYPE: DNA
<213> ORGANISM: Artificial Sequence
<220> FEATURE:
<223> OTHER INFORMATION: TMPRSS4 sense primer

<400> SEQUENCE: 13
cccaagctta tgttacagga tcctgacagt g                                31

<210> SEQ ID NO 14
<211> LENGTH: 30
<212> TYPE: DNA
<213> ORGANISM: Artificial Sequence
<220> FEATURE:
<223> OTHER INFORMATION: TMPRSS4 antisense primer

<400> SEQUENCE: 14
ccgctcgagt tacagctcag ccttccagac                                  30

<210> SEQ ID NO 15
<211> LENGTH: 21
<212> TYPE: DNA
<213> ORGANISM: Artificial Sequence
<220> FEATURE:
<223> OTHER INFORMATION: actin sense primer

<400> SEQUENCE: 15
gctcgtcgtc gacaacggct c                                           21

<210> SEQ ID NO 16
<211> LENGTH: 25
<212> TYPE: DNA
<213> ORGANISM: Artificial Sequence
<220> FEATURE:
<223> OTHER INFORMATION: actin antisense primer

<400> SEQUENCE: 16
caaacatgat ctgggtcatc ttctc                                       25

<210> SEQ ID NO 17
<211> LENGTH: 20
<212> TYPE: DNA
<213> ORGANISM: Artificial Sequence
<220> FEATURE:
<223> OTHER INFORMATION: E-cadherin sense primer

<400> SEQUENCE: 17
ggttattcct cccatcagct                                             20

<210> SEQ ID NO 18
<211> LENGTH: 19
<212> TYPE: DNA
<213> ORGANISM: Artificial Sequence
<220> FEATURE:
<223> OTHER INFORMATION: E-cadherin antisense primer

<400> SEQUENCE: 18
cttggctgag gatggtgta                                              19

<210> SEQ ID NO 19
<211> LENGTH: 384
<212> TYPE: PRT
<213> ORGANISM: Artificial Sequence
<220> FEATURE:
```

<223> OTHER INFORMATION: amino acid sequence of TMPRSS4 extracellular domain

<400> SEQUENCE: 19

```
Lys Val Ile Leu Asp Lys Tyr Tyr Phe Leu Cys Gly Gln Pro Leu His
1               5                   10                  15

Phe Ile Pro Arg Lys Gln Leu Cys Asp Gly Glu Leu Asp Cys Pro Leu
            20                  25                  30

Gly Glu Asp Glu Glu His Cys Val Lys Ser Phe Pro Glu Gly Pro Ala
        35                  40                  45

Val Ala Val Arg Leu Ser Lys Asp Arg Ser Thr Leu Gln Val Leu Asp
50                  55                  60

Ser Ala Thr Gly Asn Trp Phe Ser Ala Cys Phe Asp Asn Phe Thr Glu
65                  70                  75                  80

Ala Leu Ala Glu Thr Ala Cys Arg Gln Met Gly Tyr Ser Ser Lys Pro
                85                  90                  95

Thr Phe Arg Ala Val Glu Ile Gly Pro Asp Gln Asp Leu Asp Val Val
            100                 105                 110

Glu Ile Thr Glu Asn Ser Gln Glu Leu Arg Met Arg Asn Ser Ser Gly
        115                 120                 125

Pro Cys Leu Ser Gly Ser Leu Val Ser Leu His Cys Leu Ala Cys Gly
    130                 135                 140

Lys Ser Leu Lys Thr Pro Arg Val Val Gly Glu Glu Ala Ser Val
145                 150                 155                 160

Asp Ser Trp Pro Trp Gln Val Ser Ile Gln Tyr Asp Lys Gln His Val
                165                 170                 175

Cys Gly Gly Ser Ile Leu Asp Pro His Trp Val Leu Thr Ala Ala His
            180                 185                 190

Cys Phe Arg Lys His Thr Asp Val Phe Asn Trp Lys Val Arg Ala Gly
        195                 200                 205

Ser Asp Lys Leu Gly Ser Phe Pro Ser Leu Ala Val Ala Lys Ile Ile
    210                 215                 220

Ile Ile Glu Phe Asn Pro Met Tyr Pro Lys Asp Asn Asp Ile Ala Leu
225                 230                 235                 240

Met Lys Leu Gln Phe Pro Leu Thr Phe Ser Gly Thr Val Arg Pro Ile
                245                 250                 255

Cys Leu Pro Phe Phe Asp Glu Glu Leu Thr Pro Ala Thr Pro Leu Trp
            260                 265                 270

Ile Ile Gly Trp Gly Phe Thr Lys Gln Asn Gly Gly Lys Met Ser Asp
        275                 280                 285

Ile Leu Leu Gln Ala Ser Val Gln Val Ile Asp Ser Thr Arg Cys Asn
    290                 295                 300

Ala Asp Asp Ala Tyr Gln Gly Glu Val Thr Glu Lys Met Met Cys Ala
305                 310                 315                 320

Gly Ile Pro Glu Gly Gly Val Asp Thr Cys Gln Gly Asp Ser Gly Gly
                325                 330                 335

Pro Leu Met Tyr Gln Ser Asp Gln Trp His Val Val Gly Ile Val Ser
            340                 345                 350

Trp Gly Tyr Gly Cys Gly Pro Ser Thr Pro Gly Val Tyr Thr Lys
        355                 360                 365

Val Ser Ala Tyr Leu Asn Trp Ile Tyr Asn Val Trp Lys Ala Glu Leu
    370                 375                 380
```

<210> SEQ ID NO 20

```
<211> LENGTH: 1242
<212> TYPE: DNA
<213> ORGANISM: Artificial Sequence
<220> FEATURE:
<223> OTHER INFORMATION: sequence of TMPRSS4 extracellular domain

<400> SEQUENCE: 20
gggtgacaat ctcagctcca ggctacaggg agaccgggag gatcacagag ccagcatgtt      60
acaggatcct gacagtgatc aacctctgaa cagcctcgat gtcaaacccc tgcgcaaacc     120
ccgtatcccc atggagacct tcagaaaggt ggggatcccc atcatcatag cactactgag     180
cctggcgagt atcatcattg tggttgtcct catcaaggtg attctggata aatactactt     240
cctctgcggg cagcctctcc acttcatccc gaggaagcag ctgtgtgacg gagagctgga     300
ctgtccccttg ggggaggacg aggagcactg tgtcaagagc ttccccgaag ggcctgcagt     360
ggcagtccgc ctctccaagg accgatccac actgcaggtg ctggactcgg ccacagggaa     420
ctggttctct gcctgtttcg acaacttcac agaagctctc gctgagacag cctgtaggca     480
gatgggctac agcagcaaac ccacttttcag agctgtggag attggcccag accaggatct     540
ggatgttgtt gaaatcacag aaaacagcca ggagcttcgc atgcggaact caagtgggcc     600
ctgtctctca ggctccctgg tctccctgca ctgtcttgcc tgtgggaaga gcctgaagac     660
cccccgtgtg gtgggtgggg aggaggcctc tgtggattct tggccttggc aggtcagcat     720
ccagtacgac aaacagcacg tctgtggagg gagcatcctg gaccccccact gggtcctcac     780
ggcagcccac tgcttcagga acataccga tgtgttcaac tggaaggtgc gggcaggctc     840
agacaaactg ggcagcttcc catccctggc tgtggccaag atcatcatca ttgaattcaa     900
ccccatgtac cccaaagaca atgacatcgc cctcatgaag ctgcagttcc cactcacttt     960
ctcaggcaca gtcaggccca tctgtctgcc cttctttgat gaggagctca ctccagccac    1020
cccactctgg atcattggat ggggctttac gaagcagaat ggagggaaga tgtctgacat    1080
actgctgcag gcgtcagtcc aggtcattga cagcacacgg tgcaatgcag acgatgcgta    1140
ccaggggggaa gtcaccgaga agatgatgtg tgcaggcatc ccggaagggg gtgtggacac    1200
ctgccagggt gacagtggtg ggcccctgat gtaccaatct ga                       1242

<210> SEQ ID NO 21
<211> LENGTH: 20
<212> TYPE: DNA
<213> ORGANISM: Artificial Sequence
<220> FEATURE:
<223> OTHER INFORMATION: BglI primer

<400> SEQUENCE: 21
taagatctgg ggtgacaatc                                                   20

<210> SEQ ID NO 22
<211> LENGTH: 19
<212> TYPE: DNA
<213> ORGANISM: Artificial Sequence
<220> FEATURE:
<223> OTHER INFORMATION: SalI primer

<400> SEQUENCE: 22
gtcgacgtca gattggtac                                                    19
```

ANTICANCER DRUG COMPRISING INHIBITOR OF TMPRSS4

CROSS-REFERENCE TO RELATED APPLICATIONS

This application is a 371 of PCT/KR2006/004702, filed Nov. 10, 2006, which claims the benefit of Korean Patent Application No. 10-2006-0048685, filed May 30, 2006, the entire contents of each of which are incorporated herein by reference.

TECHNICAL FIELD

The present invention relates to an anticancer agent comprising TMPRSS4 (transmembrane protease, serine 4) inhibitor as an effective ingredient, more precisely an anticancer agent comprising the inhibitor of the TMPRSS4 activity as an effective ingredient.

BACKGROUND ART

A protease is a critical factor involved in neoplastic disorders and cancer and thus it gets importance more than ever. Cell growth, angiogenesis, invasion, migration, metastasis, survival, expansion and progression of tumor cells depend on proteolytic activities and cell signaling regulation of a protease. For example, the unregulated protease is characteristically involved in degradation and remodeling of an extracellular matrix forming an intercellular space matrix and the basement membrane, by which tumor cells are permeated into nearby tissues locally and further transferred to remote areas. Invasion and metastasis of tumor cells are very important indexes to predict and determine the prognosis of cancer. Therefore, a gene involved in regulation of metastasis can be not only used as a prognostic marker but also be an important target for cancer therapy. The representative metastasis related genes are MMPs (matrix metalloproteinases), cathepsin B, cathepsin D and uPA (urokinase plasminogen activator) containing serine protease (DeClerck; Y. A. and Imeren, S. *Eur. J. Cancer* 30A(14):2170-2180, 1994).

In particular, the functions of MMPs in relation to tumor invasion and metastasis have been best known. MMPs are members of zinc-dependent endopeptidase according to their structures, which are over-expressed in tumor microenvironment and able to decompose almost every extracellular matrix protein components. MMPs play a key role not only in cancer progression, that is invasion into the basement membrane and stroma, infiltration into blood vessel, metastasis, etc, but also in cell proliferation, growth factor release and cell migration as well (Stetler-Stevenson, W. G., Yu, A. E. *Semin. Cancer Biol.* 11(2):143-152, 2001). MMP has been reported to be over-expressed in tissues of various tumors such as breast cancer, prostatic carcinoma, ovarian cancer, lung cancer, large intestine cancer, and pancreas cancer. The high expressions of various MMP family members have been confirmed to be closely related to tumor aggressiveness (Nelson, A. R., et al., *J. Clin. Oncol.* 18(5):1135-1149, 2000). For example, MMP-1 and MMP-7 are the potential prognostic factors for large intestine cancer. Some MMP inhibitors have been proved to have metastasis inhibiting effect in pre-clinical phase and clinical phase.

It was also reported that the high expressions of uPA and uPAR (urokinase plasminogen activator receptor) in primary tumors were closely related to malignant prognosis. In addition, metastasis was induced by uPA in a cancer metastasis animal model and accordingly an uPA inhibitor could inhibit metastasis to some degree (Andreasen, P. A. et al., *Int. J. Cancer* 72(1):1-22, 1997). So, uPA seems to be a powerful and independent prognostic marker and at the same time be a potential target for the inhibition of invasion and metastasis (Andreasen P. A. et al., *Int. J. Cancer* 72(1):1-22, 1997). The cancer-related activities of other serine proteases have been comparatively less understood.

Recently, TTSP family (type II transmembrane serine protease family) has been newly identified as a serine protease family, which is over-expressed in prostatic carcinoma and ovarian cancer cells (Netzel-Arnett, S., et al., *Cancer Metastasis Rev.* 22(2-3):237-258, 2003). TMPRSS4 has been identified as a new member of type II TTSP family and confirmed to be expressed in pancreas cancer, large intestine cancer, and stomach cancer cells (Wallrapp, C., et al., *Cancer Res.* 15:60(10):2602-2606, 2000). TMPRSS4 is composed of 437 amino acids and its amino acid sequence is presumed to have trypsin-like activity. TMPRSS4 is bound to membrane by signal-anchor sequence of N-terminal and its extracellular region containing serine protease domain is glycosylated (Wallrapp, C., et al., *Cancer Res.* 15:60(10):2602-2606, 2000). It is also presumed that TMPRSS4 is involved in invasion and metastasis of pancreas cancer cells. However, a contradict result has been reported earlier saying that recombinant TMPRSS4 expression did not affect cancer invasion and progression in in vitro and in vivo pancreas cancer models (Wallrapp, C., et al., *Cancer Res.* 15:60(10):2602-2606, 2000). Thus, full explanations on the exact functions and systems of TMPRSS4 in relation to cancer cell growth, invasion and metastasis have not been given, yet.

DISCLOSURE

Technical Problem

It is an object of the present invention to provide an anticancer agent containing the inhibitor of TMPRSS4 playing an important role in cancer cell invasion as an effective ingredient.

Technical Solution

The present inventors constructed TMPRSS4 expression inhibitor and accordingly completed this invention by confirming that cancer cell invasion and growth were inhibited in the cancer cell lines transformed with the constructed inhibitor.

To achieve the object, the present invention provides an anticancer agent containing TMPRSS4 inhibitor as an effective ingredient.

The present invention also provides DNA encoding TMPRSS4-specific siRNA.

The present invention further provides a recombinant expression vector containing the DNA.

The present invention also provides a cell line transformed with the recombinant expression vector.

The present invention provides a treatment method for cancer comprising the step of administrating the above anticancer agent to a cancer patient by effective dosage.

The present invention also provides a screening method for anticancer agent candidates.

Hereinafter, the present invention is described in detail.

The present inventors performed RT-PCR with normal and cancer tissues to investigate TMPRSS4 expression in cancer tissues. As a result, TMPRSS4 expression was higher in cancer tissues than in normal tissues (see FIG. 1). The expressions of TMPRSS4 in large intestine cancer (HCT15, HCT116, HT29, COLO205, SW480, SW620, Caco2 and WiDr), lung cancer (NCI-H266, NCI-H460, NCI-H322 and A549), breast cancer (MCF-7) and brain cancer (U87MG) cell lines were also investigated. As a result, even though the expression patterns varied from cell lines, the expressions of TMPRSS4 in such cancer cell lines as large intestine cancer, lung cancer, and breast cancer were significantly high, compared with in normal HUVEC (Human Umbilical Vein Endothelial Cell) line (see FIG. 2). Then, the present inventors synthesized siRNAs (SiRNA-TMPRSS4-01, siRNA-TMPRSS4-02 and siRNA-TMPRSS4-03) targeting the expression of TMRPSS4. 293T cells were transformed with the recombinant TMPRSS4 expression vector and the synthesized siRNA and the inhibition of TMPRSS4 expression was investigated at protein level. As a result, siRNA synthesized in the present invention was confirmed to inhibit TMPRSS4 expression effectively (see FIG. 3). Among the synthesized siRNAs, SiRNA-TMPRSS4-01 and siRNA-TMPRSS4-02 were introduced into the lung cancer cell line NCI-H322, which was one of TMPRSS4 over-expressing cell lines, followed by invasion assay. As a result, the invasion capacity was inhibited in the above cancer cell line, compared with that in control (see FIG. 4). The level of cell migration was investigated during the invasion assay and as a result cell migration was 33~60% inhibited, compared with that in control (see FIG. 5). Considering that the transformation efficiency was 60%, the observed inhibition of TMPRSS4 expression indicates almost 100% inhibition of cancer cell invasion and metastasis. Therefore, TMPRSS4 was confirmed to be a crucial factor involved in cancer cell invasion and metastasis.

The present inventors constructed cell lines over-expressing TMPRSS4. The large intestine cancer cell line SW480 exhibits a low level of TMPRSS4 expression. The present inventors introduced the recombinant TMPRSS4 expression vector into the SW480 to construct SW480-T4 and SW480-T17 cell lines. RT-PCR and Western blotting were performed with those cell lines and as a result over-expression of TMPRSS4 was confirmed (see FIG. 6A and FIG. 6B). Invasion assay was also performed with the SW480-T4 and SW480-T17 cell lines. As a result, cell migration was respectively 5 fold and 14 fold higher in those cell lines than in control cell line SW480 transformed with an empty vector (see FIG. 6C). In particular, cell migration in SW480-T17 cell line was significantly high along with TMPRSS4 expression as proved by RT-PCR and Western blotting. A lung cancer cell line A549 was also transformed with the recombinant vector to construct TMPRSS4 over-expression cell lines, resulting in A549-T5 and A549-T12 cell lines. Over-expression of TMPRSS4 was confirmed by Western blotting with those cell lines (see FIG. 7A). Invasion assay was also performed with A549-T5 and A549-T12 cell lines and as a result cell migration in those cell lines was significantly increased, compared with in control cell line transformed with an empty vector (see FIG. 7B). From the above results, it was confirmed that TMPRSS4 plays a critical role in cancer cell invasion and metastasis.

To investigate the effect of the inhibition of TMPRSS4 expression on cancer cell growth, a lung cancer cell line NCI-H322 was transformed with siRNA and then cell proliferation was investigated in the presence or absence of serum in the culture medium. When the cell line was cultured in the presence of serum, cell growth was not inhibited for 72 hours (see FIG. 8). On the contrary, when the cell line was cultured in the serum-free medium, cell growth was inhibited, compared with the cell growth of control cell line or cell line transformed with negative control siRNA (see FIG. 9). That is, the inhibition of TMPRSS4 expression was confirmed to be an inhibition of cancer cell growth and/or cancer cell survival. So, TMPRSS4 reduces growth factor dependent growth of cancer cells and thereby induces abnormal growth of cancer cells.

The present inventors further investigated the effect of over-expression of TMPRSS4 on cell morphology. Compared with control cells, cell spreading and lamellipoidia formed on the edges of cells were obviously observed in TMPRSS4 over-expressing cells (see FIG. 10). Actin rearrangement was also investigated by immunocytochemistry. As a result, overall distribution of actin was observed but a filament was not formed in the cell line transformed with an empty vector. In the meantime, the stress fiber was formed and the inter-cellular filopodia like structure was observed in TMPRSS4 over-expressing cell lines (SW480-T4 and SW480-T17)(see FIG. 11). The results indicate that over-expression of TMPRSS4 brings the changes of cell morphology by rearrangement of actin cytoskeleton and thereby increases cellular invasion.

To investigate if the over-expression of TMPRSS4 would be related to the regulation of expressions of important factors involved in cellular invasion, the expression of E-cadherin inducing inter-cellular attachment was measured. As a result, the expression of E-cadherin in TMPRSS4 over-expressing cell lines (SW480-T4 and SW480-T17) was reduced (see FIG. 12). Therefore, it was confirmed that the over-expression of TMPRSS4 reduced the level of E-cadherin expression and thereby reduced inter-cellular attachment and at the same time induced epithelial-mesenchymal transition as well as actin cytoskeleton rearrangement.

The present invention also provides an anticancer agent containing a TMPRSS4 inhibitor as an effective ingredient.

The TMPRSS4 inhibitor is preferably selected from a group consisting of an antisense nucleotide binding complementarily to TMPRSS4 mRNA, a small interfering RNA (referred as "siRNA" hereinafter), a substrate analogue binding to TMPRSS4 protein, an antibody and a small compound inhibiting the activity of TMPRSS4.

Antisense Nucleotide

The antisense nucleotide is recognized as a promising therapeutic agent for various human diseases. As described by Watson-Crick base-pair model, a nucleotide sequence is hybridized with a complementary sequence of DNA, immature-mRNA or mRNA to interrupt the transmission of genetic information. A target sequence specific antisense nucleotide is exceptionally multi-functional. The antisense-nucleotide is a long chain of monomers, which favors hybridization to a target RNA sequence. Numbers of reports have been recently made to prove the utility of an antisense nucleotide as a biochemical tool in study of a target protein (Rothenberg et al., *J. Natl. Cancer Inst.*, 81:1539-1544, 1999). Progress has been made in the fields of oligonucleotide synthesis, improved cell adhesion of oligonucleotide, target binding affinity and synthesis of nucleotide having resistance against nuclease, suggesting that an antisense nucleotide might be a new sort of a therapeutic agent. For example, the antisense nucleotide targeting cmyb has been used to eliminate myelogenous leukemia cells from the bone marrow of a leukemia patient (Gewirtz and Calabreta, U.S. Pat. No. 5,098,890). It is also known that an antisense nucleotide has an in vivo therapeutic effect on cytomegalovirus retinitis. An antisense nucleotide can be prepared by using TMPRSS4 mRNA sequence according to a conventional method well known to those in the art and the antisense nucleotide is expected to play a role in inhibiting TMPRSS4 by binding specifically to TMPRSS4 mRNA.

siRNA Molecule

A sense RNA and an antisense RNA together form a double stranded RNA. At this time, the sense RNA includes the same nucleotide sequence as the target sequence of 19~25 consecutive nucleotides among TMPRSS4 mRNA. And the present invention provides siRNA based on that.

The siRNA of the invention is preferably composed of the sense sequence comprising 19~25 nucleotides selected from TMPRSS4 nucleotide sequence and the antisense sequence binding complementarily to the sense RNA, and is more preferably composed of 24 nucleotides selected from a group consisting of SEQ. ID. NO: 7, NO: 9 and NO: 11, but not always limited thereto. Any double stranded RNA having the sense sequence that is able to bind complementarily to RMPRSS4 nucleotide sequence can be used. The antisense sequence herein preferably contains the complementary sequence of the sense sequence.

An inhibitor of TMPRSS4 can be selected from a group consisting of a peptide that is able to bind to the above protein, an antibody and a substrate analogue, a small compound inhibiting TMPRSS4 protein activity.

Antibody

An antibody against TMPRSS4 indicates a TMPRSS4 specific antibody that directly binds to TMPRSS4 to inhibit its activity. As a TMPRSS4 specific antibody, a polyclonal antibody or a monoclonal antibody is preferred and in particular a monoclonal antibody is more preferred. A biomarker binding antibody can be prepared by a conventional method well known to those in the art or can be purchased. For example, the antibody can be constructed, according to the conventional method known to those in the art, by injecting TMPRSS4 protein into a host. A host is selected from a group consisting of such mammals as a mouse, a rat, a lamb and a rabbit. The immunogen is intramuscularly-, intraabdominally-, or hypodermically injected. The immunogen is generally injected with an adjuvant to enhance antigenicity. Blood samples were taken from the host at regular intervals and serum exhibiting titer and specificity to the antigen was collected to separate an antibody therefrom.

Substrate Analogue

A substrate analogue (ex: peptide or non-peptide) functioning as an inhibitor of TMPRSS4 binding domain can be used as an inhibitor of TMPRSS4 activity. Particularly, the peptide analogue or non-hydrolysable peptide analogue of a short peptide substrate (U.S. Pat. No. 7,650,034), that is a TMPRSS4 substrate, can be used.

The non-hydrolysable peptide analogue can be prepared by using β-turn dipeptide core (Nagai et al., Tetrahedron. Lett. 26:647, 1985), keto-methylene sheudopeptides (Ewenson et al., *J. Med. Chem.* 29:295, 1986; Ewenson et al., in Peptides: Structure and Function (Proceedings of the 9th American Peptide Symposium) Pierce Chemical Co. Rockland, Ill., 1985), asepine (Huffman et al., in Peptides: Chemistry and Biology, G. R. Marshall ed., ESCOM Publisher: Leiden, Netherlands, 1988), benzodiazepine (Freidinger et al., in Peptides; Chemistry and Biology, G. R. Marshall ed., ESCOM Publisher: Leiden, Netherlands, 1988), β-aminoalcohol (Gordon et al., *Biochem. Biophys. Res. Commun.* 126:419 1985) and substituted gamma lactam ring (Garvey et al., in Peptides: Chemistry and Biology, G. R. Marshell ed., ESCOM Publisher: Leiden, Netherlands, 1988).

The present invention further provides a DNA encoding TMPRSS4 specific siRNA.

The DNA sequence is preferably composed of a DNA sequence encoding the siRNA sense sequence, 4~10 bp long loop sequence, and an antisense sequence complement to the DNA sequence.

The present invention also provides a recombinant expression vector containing the DNA sequence.

Herein, the recombinant expression vector is not limited to specific ones, but is preferably prepared by introducing the DNA sequence corresponding to the siRNA into a vector selected from a group consisting of the conventional siRNA expression vectors psiRNA (Invitrogen, USA), pRNA (GenScript, USA), psLentGene (Promega, USA), pSIREN (Clontech, USA), pU6shX (VectorCoreA, Korea), and pSilencer (Ambion, USA). The vector construct depends on specific environments such as transformation form, time and siRNA expression level, etc.

The vector can be introduced into the nucleus of a cell in the form of a simple plasmid DNA or a complex with a transformation reagent or a target delivery substance, or a recombinant virus vector. A virus vector herein is exemplified by retrovirus including adenovirus, adeno-associated virus and lentivirus.

The present invention also provides a cell line transformed with the recombinant expression vector.

The recombinant expression vector of the invention expressing siRNA inhibiting TMPRSS4 expression was introduced into normal cells and/or cancer cells to construct a transformed cell line. Any conventional transformation method known to those in the art can be used. The cancer cell line is preferably selected from a group consisting of HCT-15, HCT116, HT29, Colo205, SW480, SW620, Caco2, WiDr, NCI-H226, NCI-H322, NCI-H460, A549 and MCF-7, but not always limited thereto.

The anticancer agent of the present invention contains the TMPRSS4 inhibitor or the recombinant expression vector as an effective ingredient. The anticancer agent of the invention includes the TMPRSS4 inhibitor by 0.0001~50 weight part for the total weight of the agent. The anticancer agent of the invention can additionally include, in addition to the TMPRSS4 inhibitor, one or more effective ingredients exhibiting the same or, similar functions to the TMPRSS4 inhibitor.

The anticancer agent of the present invention can also include, in addition to the above-mentioned effective ingredients, one or more pharmaceutically acceptable carriers for the administration. The pharmaceutically acceptable carrier can be selected or be prepared by mixing more than one ingredients selected from a group consisting of saline, sterilized water, Ringer's solution, buffered saline, dextrose solution, maltodextrose solution, glycerol and ethanol. Other general additives such as anti-oxidative agent, buffer solution, bacteriostatic agent, etc, can be added. In order to prepare injectable solutions, pills, capsules, granules or tablets, diluents, dispersing agents, surfactants, binders and lubricants can be additionally added. The anticancer agent of the present invention can further be prepared in suitable forms for each disease or according to ingredients by following a method represented in Remington's Pharmaceutical Science (the newest edition), Mack Publishing Company, Easton Pa.

The anticancer agent of the present invention can be administered orally or parenterally (for example, intravenous, hypodermic, local or peritoneal injection). The effective dosage of the anticancer agent can be determined according to weight, age, gender, health condition, diet, administration frequency, administration method, excretion and severity of a disease. The dosage of the anticancer agent of the invention is 0.01~12.5 mg/kg per day, and preferably 1.25~2.5 mg/kg per day. Administration frequency is once a day or preferably a few times a day.

The anticancer agent of the present invention was i.v. injected to mice to investigate toxicity. As a result, it was evaluated to be a safe substance since its estimated $LD_{50}$ value was much greater than 1,000 mg/kg in mice.

The anticancer agent of the present invention can be administered singly or treated along with surgical operation, hormone therapy, chemotherapy and biological reaction regulator, to prevent and treat cancer.

The present invention also provides a treatment method for cancer including the step of administering the anticancer agent of the invention to a patient by an effective dose to inhibit metastasis and/or cancer cell growth.

The target cancer is preferably large intestine cancer, lung cancer and breast cancer, but not always limited thereto, and any cancer exhibiting over-expression of TMPRSS4 can be included.

The present invention also provides a screening method for an anticancer agent candidate.

The present invention provides a screening method comprising the following steps:
1) treating a cancer cell line with a sample compound;
2) measuring TMPRSS4 activity in the cancer cell line of the step 1); and
3) selecting a sample compound inhibiting TMPRSS4 activity by comparing the result of the step 2) with the activity in a control cell line not treated with the sample compound.

In the screening method, the sample compound of step 1) is preferably selected from a group consisting of a protein, a peptide, a natural compound, an extract, and a synthetic compound, but not always limited thereto.

In the screening method, the cancer cell line of 1) can be any cell line over-expressing TMPRSS4. For example, the cancer cell line is selected from a group consisting of large intestine cancer, lung cancer, and breast cancer cell lines but not always limited thereto and as mentioned above any cell line that over-expresses TMPRSS4 is accepted.

In the screening method, the measurement of TMPRSS4 of step 2) is performed by RT-PCR (reverse transcription polymerase chain reaction), Western blotting, ELISA (enzyme-linked immunosorbent assay) or immunoprecipitation, but not always limited thereto and any conventional protein activity measurement method that is known to those in the art can be used.

The present invention also provides a screening method comprising the following steps:
1) adding a sample compound to the reaction solution containing TMPRSS4 and TMPRSS4 substrate in vitro;
2) measuring the activity of TMPRSS4; and
3) selecting a sample compound inhibiting TMPRSS4 activity by comparing the result of the step 2) with the activity in a control cell line not treated with the sample compound.

In the screening method, the sample compound of step 1) is preferably selected from a group consisting of a protein, a peptide, a natural compound, an extract, and a synthetic compound, but not always limited thereto. The TMPRSS4 of step 1) is preferably TMPRSS4 full length protein or the extracellular domain of TMPRSS4 (54~437 amino acid).

In the screening method, the TMPRSS4 substrate of step 2) is preferably t-butyloxycarbonyl-Gln-Ala-Arg-7-amido-4-methylcoumarin, but not always limited thereto and any TMPRSS4 substrate known to those in the art can be accepted. The measurement of TMPRSS4 activity in step 2) can be performed by measuring the decomposition of the TMPRSS4 substrate. The present inventors measured the enzyme activity of TMPRSS4 using the synthetic substrate of TMPRSS4, t-butyloxycarbonyl-Gln-Ala-Arg-7-amido-4-methylcoumarin (see FIG. 13). The measurement of TMPRSS4 activity was performed by Western blotting using a TMPRSS4 substrate specific antibody, radio-labeling to TMPRSS4 substrate or immunoprecipitation using a TMPRSS4 substrate specific antibody. TMPRSS4 substrate was fluorescence-labeled and then fixed on a 96-well plate. When a sample compound and TMPRSS4 added thereto, if the substrate is decomposed by TMPRSS4, fluorescence will not be detected. But if the enzyme activity of TMPRSS4 is inhibited and thus substrate is not decomposed, fluorescence will be detected, by which a candidate for an anticancer agent will be screened. When an antibody specific to a degradation product of TMPRSS4 substrate is added, if the enzyme activity of TMPRSS4 is inhibited by the sample compound, the degradation product of the substrate will be reduced, which can be screened by Western blotting or ELISA. But, the screening method is not limited thereto, and any enzyme activity measurement method known to those in the art can be used. The applicable TMPRSS4 substrate can be selected among substrates described in the following patent documents:

U.S. Pat. No. 6,750,034;
US 2003/0119168 A;
US 2004/0001801 A;
WO 01/57194 A;
WO 2004/074510 A; and
WO 2004/097034 A.

The above documents can be used as references for the present invention.

DESCRIPTION OF DRAWINGS

The application of the preferred embodiments of the present invention is best understood with reference to the accompanying drawings, wherein:

FIG. 4 is a set of photographs illustrating the invasion capacity of NCl-H322 cell lines transformed with siRNA.

A: Expression of TMPRSS4 in TMPRSS4 over-expressing cell lines, investigated by Western blotting; and B: Invasion of TMPRSS4 over-expressing cell lines, investigated by matrigel assay.

Figure 8:
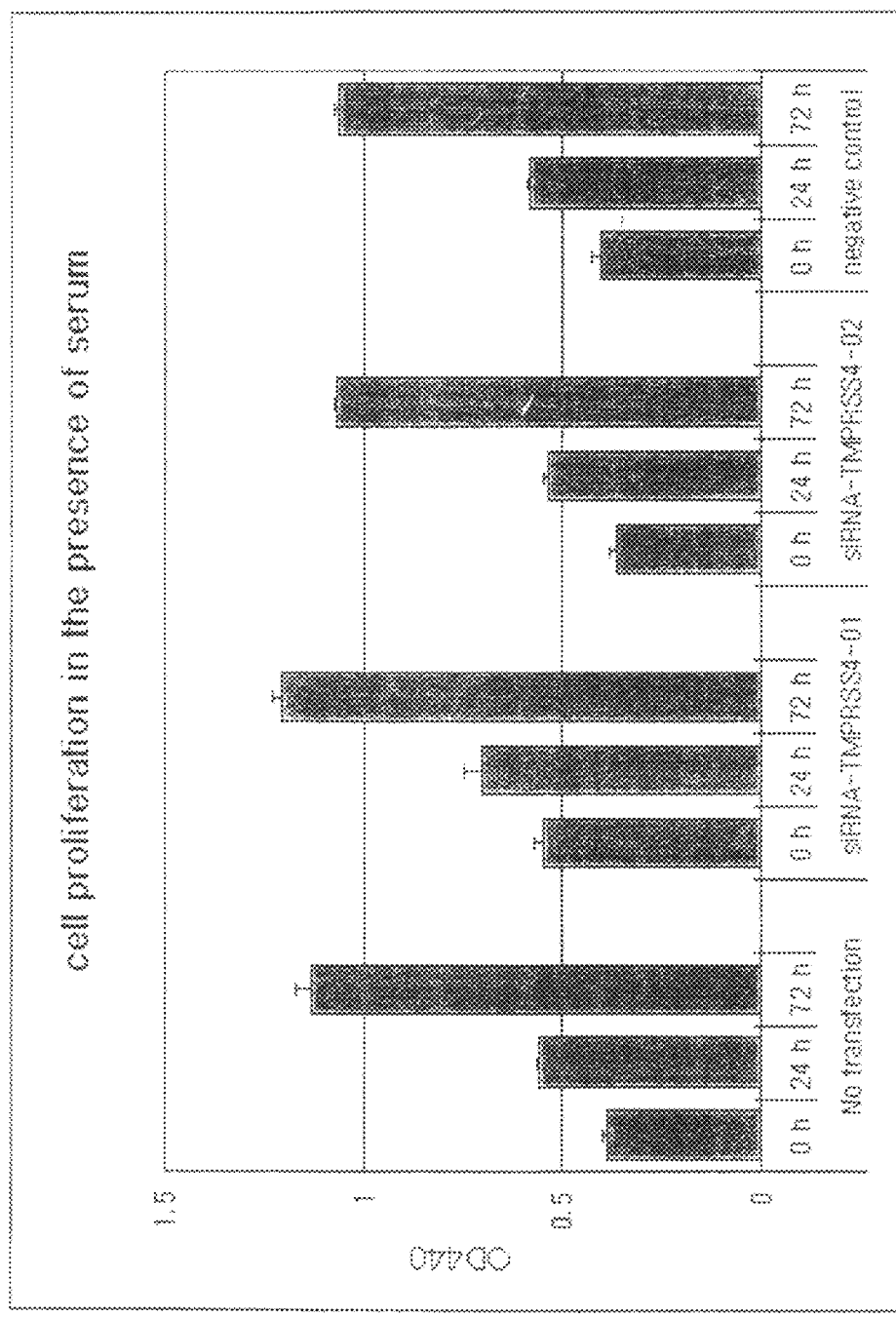

FIG. 8 is a graph illustrating the cell proliferation of NCI-H322 cell lines transformed with siRNA in a serum containing medium.

Figure 9:
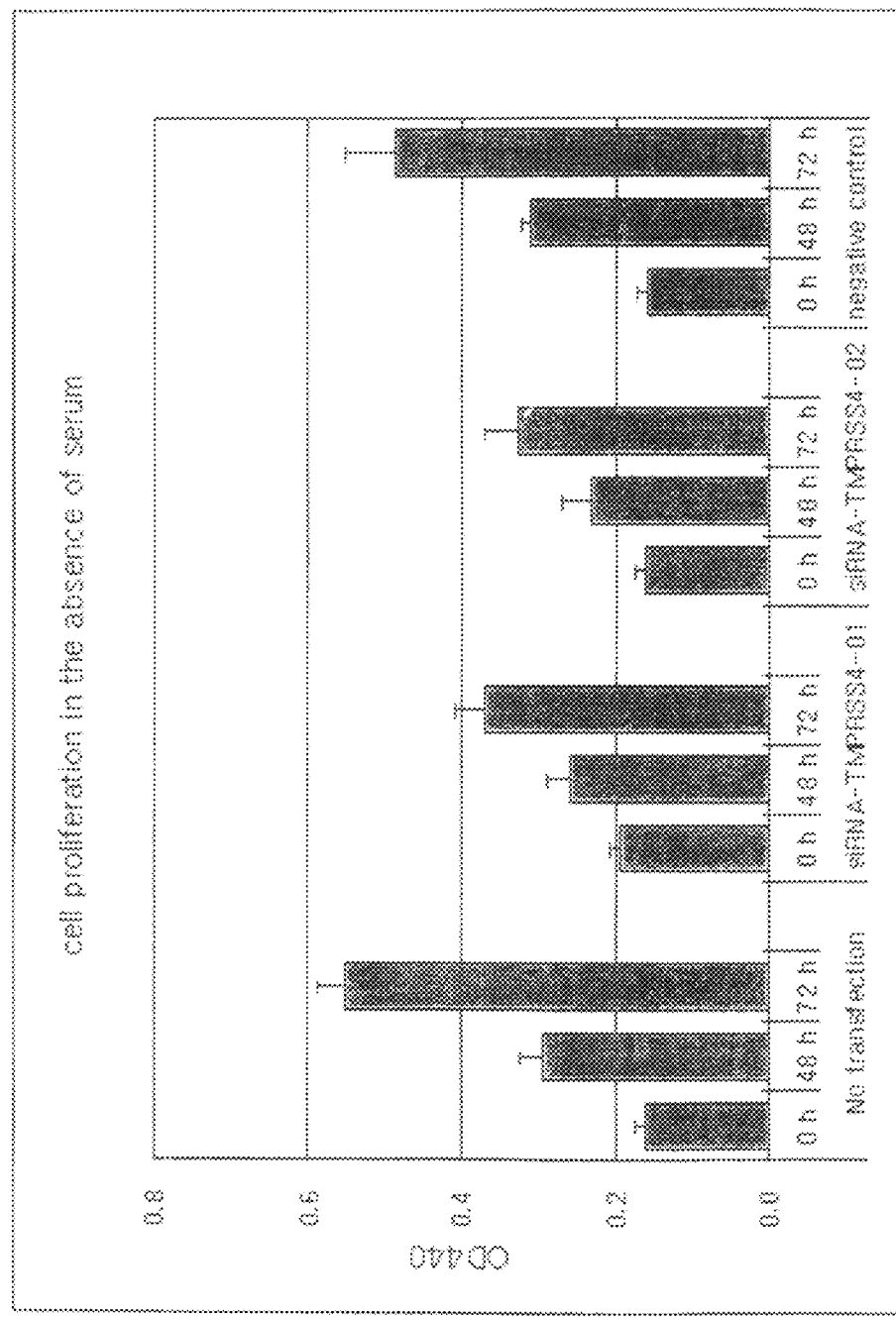

FIG. 9 is a graph illustrating the cell proliferation of NCI-H322 cell lines transformed with siRNA in a serum-free medium.

Figure 10:
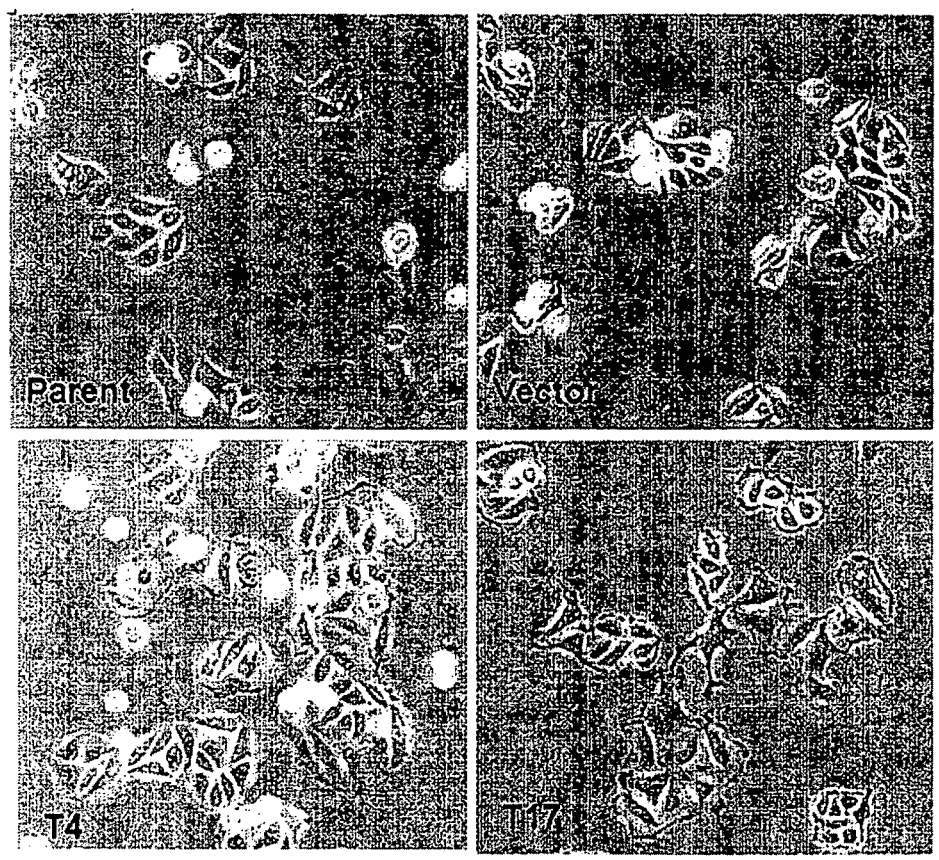

FIG. 10 is a set of photographs illustrating morphologies of TMPRSS4 over-expressing cell lines (SW480).

Figure 11:
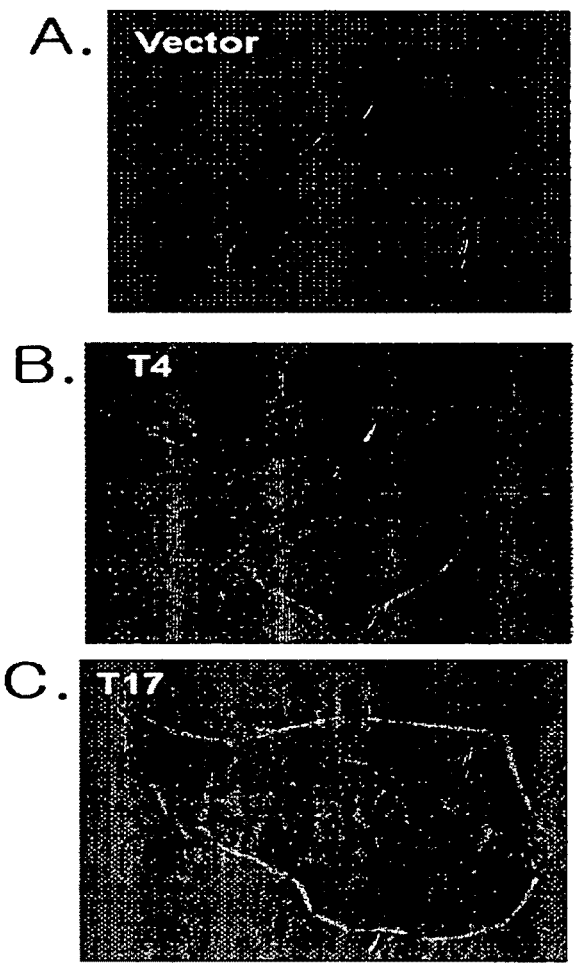

FIG. 11 is a set of photographs illustrating intracellular actin rearrangement examined by immunocytochemistry.

A: SW480 cell line transformed with an empty vector;

B: SW480-T4 cell line; and

C: SW380-T17 cell line.

Figure 12:
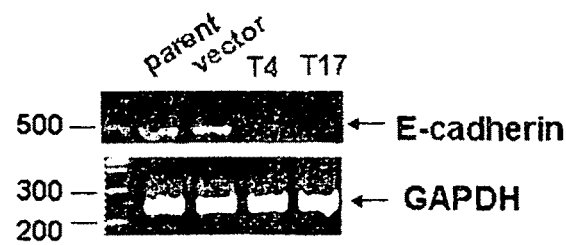

FIG. 12 is a set of photographs illustrating the result of RT-PCR investigating the expression of E-cadherin in TMPRSS4 over-expressing cell lines (SW480).

Figure 13:
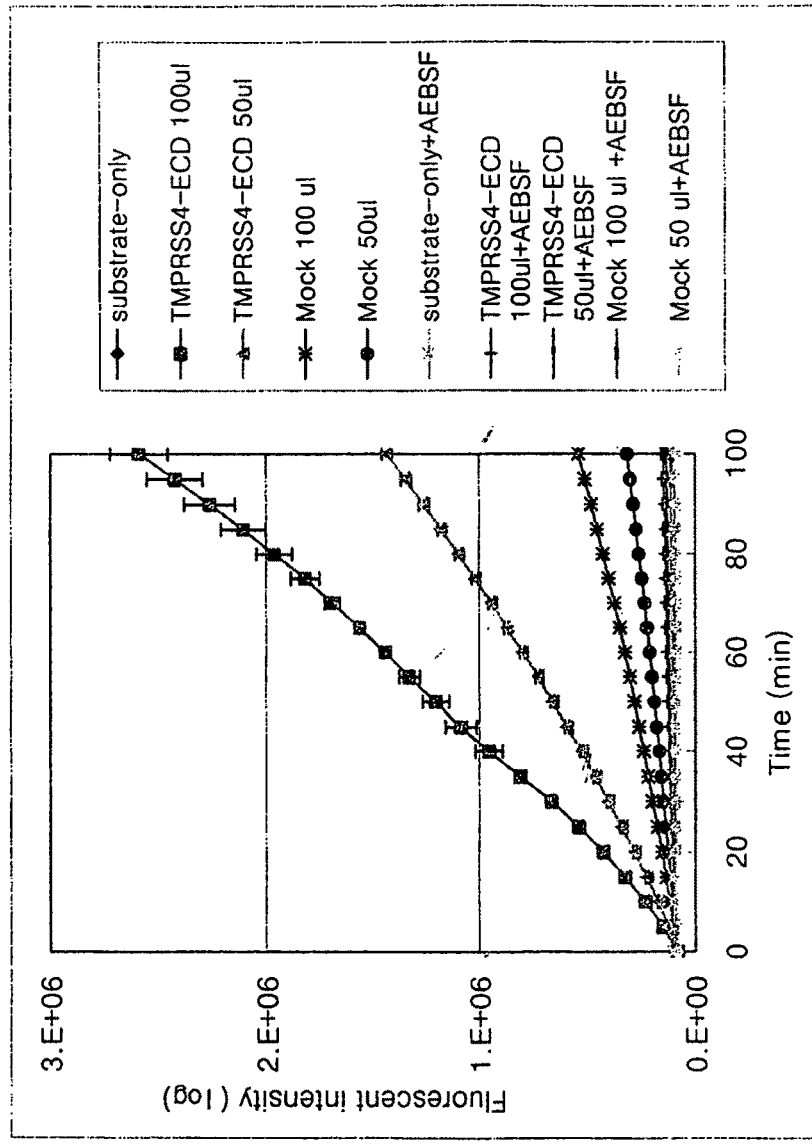

FIG. 13 is a graph illustrating the degradation of the synthetic substrate of TMPRSS4 extracellular domain.

MODE FOR INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXAMPLE 1

TMPRSS4 Expression

<1-1> TMPRSS4 Expression in Tumor Tissue

To examine if TMPRSS4 was over-expressed in cancer cells compared with in normal cells, the present inventors performed RT-PCR to investigate TMPRSS4 expression in lung cancer patient tissues. 8 lung cancer tissues and normal tissues were provided by Korea Cancer Center Hospital (Seoul, Korea), and then total RNA was extracted by using TRIZOL® (Invitrogen, USA). 1 μg of RNA was denatured at 70° C. for 10 minutes, to which oligo dT primer and SuperScript II reverse transcriptase (Invitrogen, USA) were added, followed by reverse transcription reaction at 42° C. for 1 hour. The reverse transcriptase was inactivated by heating at 90° C. for 2 minutes. To amplify 453 bp long TMPRSS4 fragment, TMPRSS4 fragment forward primer (5'-TAC AAT GTC TGG AAG GCT GAG-3') represented by SEQ. ID. NO: 1 and TMPRSS4 fragment reverse primer (5'-TTC TTG CTC TAG TAG GCT TGG-3') represented by SEQ. ID. NO: 2 were used. The primers were TMPRSS4 specific, which means they were constructed carefully not to amplify other members of type II transmembrane serine protease. PCR was performed as follows; predenaturation at 94° C. for 5 minutes, denaturation at 94° C. for 30 seconds, annealing at 54° C. for 30 seconds, polymerization at 72° C. for 30 seconds, 24 cycles from denaturation to polymerization, and final extension at 72° C. for 5 minutes.

Figure 1:
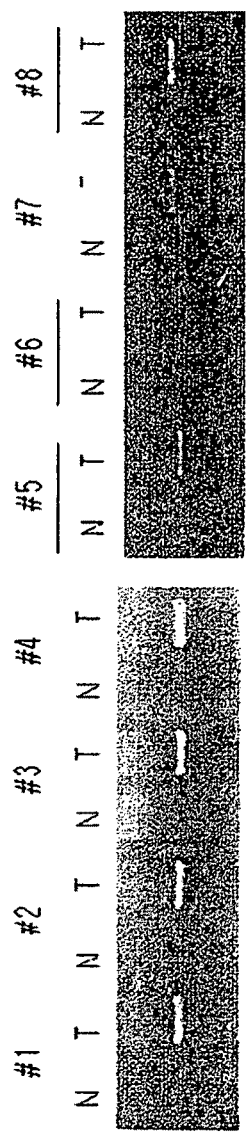
FIG. 1 is a set of photographs illustrating the results of RT-PCR showing the expressions of TMPRSS4 in normal and tumor tissues.
N: Normal tissue; and
T: Tumor tissue.

AS a result, it was confirmed that the expression of TMPRSS4 was significantly increased in cancer tissues, compared with in normal tissues (FIG. 1).

<1-2> TMPRSS4 Expression in Cancer Cell Line

The present inventors extracted total RNA from each cancer cell line (colon cancer cell line: HCT15, HCT116, HT29, COLO205, SW480, SW620, Caco2 and WiDr; lung cancer cell line: NCI-H226, NCI-H322, NCI-H460 and A549; breast cancer cell line: MCF-7; brain cancer cell line: U87MG) by using High Pure RNA Isolation kit (Roche, Mannheim, Germany). The culture conditions for each cell line were as follows. All the human cell lines were provided from American Type Culture Collection (USA). WiDr, Caco-2 and U-87MG cell lines were cultured in MEM (minimal essential medium: GIBCO, USA) supplemented with 10% FBS (fetal bovine serum: GIBCO, USA), penicillin-streptomycin, L-glutamine, sodium pyruvate, and nonessential amino acids. HCT116, HT29, Colo205, SW480, SW620, HCT15, NCI-H322, A549, NCl-H460, NCl-H226 and MCF-7 cell lines were cultured in RPMI1640 (GIBCO, USA) supplemented with 10% FBS, penicillin-streptomycin, L-glutamine, sodium pyruvate, HEPES, and glucose. 293T cell line was cultured in DMEM (Dulbeco's Modified Eagle Medium: GIBCO, USA) supplemented with 10% FBS, penicillin-streptomycin, L-glutamine, sodium pyruvate and glucose. HUVEC (Human Umbilical Vein Endothelial Cell) cell line was cultured using EGM-2 BulletKit (Cambrex Bio Science Walkersville, Inc., USA) according to the manufacturer's instruction. Cell lines were cultured in a 37° C. 5% $CO_2$ incubator and the cell lines were taken care not to be contaminated by mycoplasma. 5 μg of total RNA extracted from each cell line cultured as the above was denatured at 70° C. for 10 minutes, to which oligo dT primer and SuperScript II reverse transcriptase (Invitrogen, USA) were added, followed by reverse transcription reaction at 42° C. for one hour. The reverse transcriptase was inactivated by heating at 90° C. for 2 minutes. To amplify cDNA by PCR, TMPRSS4 forward primer (5'-CCG ATG TGT TCA ACT GGA AG-3') represented by SEQ. ID. NO: 3 and TMPRSS4 reverse primer (5'-CCC ATC CAA TGA TCC AGA GT-3') represented by SEQ. ID. NO: 4 were used. For the control group GAPDH, GAPDH forward primer (5'-TGA TGA CAT CAA GAA GGT GGT GAA G-3') represented by SEQ. ID. NO: 5 and GAPDH reverse primer (5'-TCC TTG GAG GCC ATG TGG GCC AT-3') represented by SEQ. ID. NO: 6 were used. PCR was performed as follows; predenaturation at 94° C. for 2 minutes, denaturation at 94° C. for 30 seconds, annealing at 59° C. for 30 seconds, polymerization at 72° C. for 2 minutes, 30 cycles from denaturation to polymerization, and final extension at 72° C. for 10 minutes. PCR products were electrophoresed on 2% agarose gel or 8% polyacrylamide gel. Every reaction was repeated at least two times.

Figure 2:
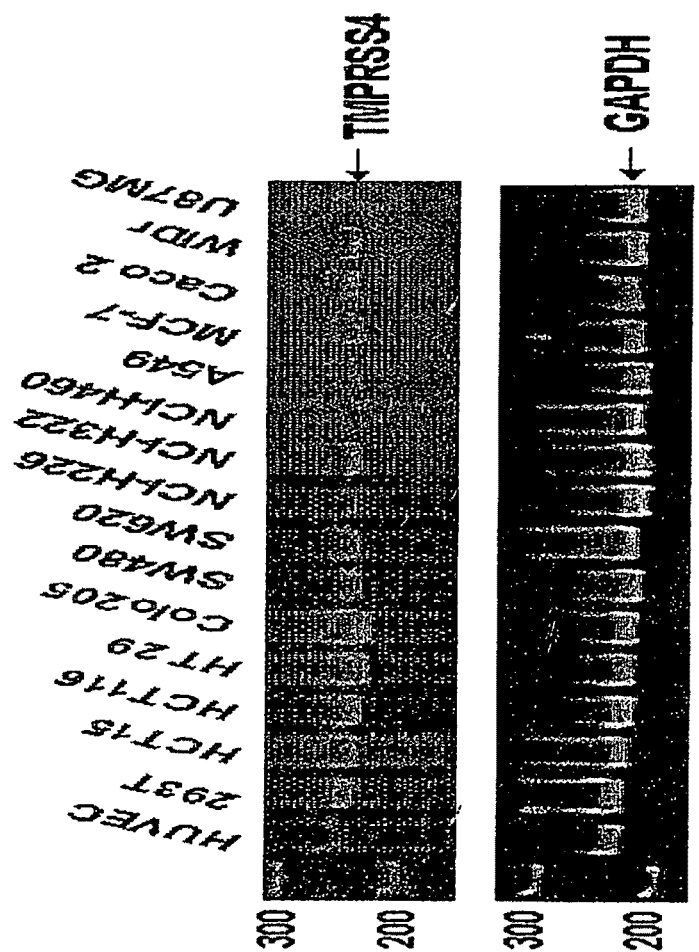
FIG. 2 is a set of photographs illustrating the results of RT-PCR investigating the expression of TMPRSS4 in each cancer cell line.

As a result, the level of TMPRSS4 expression was high in every cancer cell lines including colon cancer, lung cancer and breast cancer cell lines (FIG. 2). Even though the level of TMPRSS4 expression was different in each cancer cell line, the expression of TMPRSS4 was high in cancer cell lines, compared with in HUVEC (Human Umbilical Vein Endothelial Cell).

EXAMPLE 2

Effect of TMPRSS4-Specific Small Interfering RNA (Referred as "siRNA" Hereinafter) on Cancer Metastasis <2-1> Construction of siRNA To investigate TMPRSS4 expression, the present inventors prepared synthetic siRNA dimeric oligomer. Three kinds of chemically synthesized siRNA dimers were provided from Invitrogen (USA). siRNA dimer sequences are as follows: siRNA-TMPRSS4-01: 5'-AAG UUG UCG AAA CAG GCA GAG AAC C-3' (SEQ. ID. NO: 7), 5'-GGU UCU CUG CCU GUU UCG ACA ACU U-3' (SEQ. ID. NO: 8); siRNA-TMPRSS4-02: 5'-CAG ACG UGC UGU UUG UCG UAC UGG A-3' (SEQ. ID. NO: 9), 5'-UCC AGU ACG ACA AAC AGC ACG UCU G-3' (SEQ. ID. NO: 10); siRNA-TMPRSS4-03: 5'-UAU GUU UCC UGA AGC AGU GGG CUG C-3' (SEQ. ID. NO: 11), 5'-GCA GCC CAC UGC UUC AGG AAA CAU A-3' (SEQ. ID. NO: 12) (Table 1). Non-specific siRNA dimeric oligomer was used as a negative control.

TABLE 1 siRNA sequence

| Name | Sequence | SEQ. ID. No. |
|---|---|---|
| siRNA-TMPRSS4-01 | 5'-AAG UUG UCG AAA CAG GCA GAG AAC C-3' | 7 |
| | 5'-GGU UCU CUG CCU GUU UCG ACA ACU U-3' | 8 |
| siRNA-TMPRSS4-02 | 5'-CAG ACG UGC UGU UUG UCG UAC UGG A-3' | 9 |
| | 5'-UCC AGU ACG ACA AAC AGC ACG UCU G-3' | 10 |
| siRNA-TMPRSS4-03 | 5'-UAU GUU UCC UGA AGC AGU GGG CUG C-3' | 11 |
| | 5'-GCA GCC CAC UGC UUC AGG AAA CAU A-3' | 12 |

<2-2> Construction of Plasmid and cDNA pCMV-myc tag expression vector was provided from Stratagene Co. (USA). The full-length human TMPRSS4 cDNA was provided from National Genome Information Center (NGIC, Daejon, Korea). PCR was performed using TMPRSS4 as a template. To amplify TMPRSS4, TMPRSS4 forward primer (5'-CCC AAG CTT ATG TTA CAG GAT CCT GAC AGT G-3') represented by SEQ. ID. NO: 13 and TMPRSS4 reverse primer (5'-CCG CTC GAG TTA CAG CTC AGC CTT CCA GAC-3') represented by SEQ. ID. NO: 14 were used. PCR was performed as follows; predenaturation at 94° C. for 2 minutes, denaturation at 94° C. for 30 seconds, annealing at 59° C. for 30 seconds, polymerization at 72° C. for 2 minutes, 30 cycles from denaturation to polymerization, and final extension at 72° C. for 10 minutes. PCR product was digested with Hind III and Xho I, and introduced into pCMV-myc tag expression vector, resulting in the construction of "pCMV-myc-TMPRSS4" vector. The additional vector prepared was confirmed as wild type by base sequencing. Every plasmid was introduced into E. coli and after transformation they were isolated by using Plasmid midi kit (QIAGEN, Germany).

<2-3> Transformation

3 μg of pCMV-myc-TMPRSS4 expression vector prepared in Example <2-2>, 200 pmol of siRNA dimer prepared in Example <2-1>, and 5 μl of Lipofectamine™ 2000 (Invitrogen, USA) were mixed in 2.5 ml of Opti-MEM, with which 293T cells were transformed according to the manufacturer's instruction (Invitrogen, USA). 293T cells were distributed in a 6-well plate at the concentration of 3×10$^5$ cells/well. 48 hours after transformation, the cells were lysed, followed by Western blotting.

<2-4> Western Blotting

The expression level of TMPRSS4 protein was evaluated by measuring the expression of myc-tagged TMPRSS4 protein by Western blotting. Western blotting was performed as follows. The transformed cells were lysed with RIPA buffer (10 mM Tris, pH7.2, 150 mM NaCl, 1% deoxycholate, 1% Triton X-100, 0.1% SDS, 1 mM sodium orthovanadate, 50 mM NaF, 1 mM PMSF, complete protease inhibitor) and the lysate was quantified by Bradford method (Bradford, M M., Anal. Biochem. 72:248-254, 1976). The protein samples were mixed with SDS buffer and 50 μg of the lysate and then heated, followed by 10% SDS-PAGE gel electrophoresis. The separated protein was transferred to nitrocellulose membrane and blocked by 5% skim milk. The protein was reacted with myc antibody 4A6 (1:1000; Upstate, Lake Placid, USA) or anti-actin antibody (1:1000; Santa Cruz Biotechnology, Santa Cruz, USA) and then further reacted with horseradish peroxidase labeled secondary antibody. The protein was treated with ECL kit (ECL Plus, Amersham, USA) according to the manufacturer's instruction.

Figure 3:
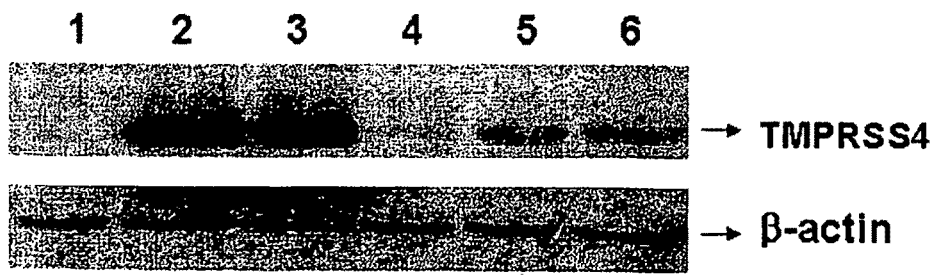
FIG. 3 is a set of photographs illustrating the results of Western blotting investigating the expression of TMPRSS4 by siRNA in 293T cells.
Lane 1: 293T cells;
Lane 2: 293T cells transformed with pCMV-myc-TMPRSS4;
Lane 3: pCMV-myc-TMPRSS4, negative control siRNA-transformed 293T cells;
Lane 4: pCMV-myc-TMPRSS4, siRNA-TMPRSS4-01-transformed 293T cells;
Lane 5: pCMV-myc-TMPRSS4, siRNA-TMPRSS4-02-transformed 293T cells; and
Lane 6: pCMV-myc-TMPRSS4, siRNA-TMPRSS4-03-transformed 293T cells.

As a result, three kinds of synthetic siRNAs exhibited TMPRSS4 expression inhibiting effect (FIG. 3).

<2-6> Invasion Assay

The present inventors selected two of three siRNAs, siRNA-TMPRSS4-01 and siRNA-TMPRSS4-02 to transform NCI-H322 which was a TMPRSS4 over-expressing lung cancer cell line. The NCI-H322 cell line was distributed in a 6-well plate and cultured until the population took 50% of the area. 180 pmol of siRNA dimer and 6 μl of Lipofectamine™ 2000 (Invitrogen, USA) were mixed in 2.5 ml of Opti-MEM, followed by transformation according to the manufacturer's instruction (Invitrogen, USA). At this time, siRNA having a random nucleotide sequence was used as a negative control. Transformation efficiency was measured by using fluorescence labeled RNA. As a result, transformation efficiency was confirmed to be approximately 60%. Matrigel assay was performed by using the transformed NCI-H322 cell line as follows. The porous membrane of the 24-well trans-well plate (8 μm pore size; Costar, Corning, USA) was coated with 100 μl of matrigel (BD Biosciences, Bedford, USA) diluted in a serum-free medium at the concentration of 250 μg/ml, at room temperature for one hour. The bottom of the trans-well plate was coated with 100 μl of human collagen type I (Chemicon, Temecula, USA) as a chemoattractant at the concentration of 10 μg/ml. 1×10$^5$ cells cultured in a serum-free medium were distributed in the upper chamber, followed by culture for 72 hours in a 37° C. 5% $CO_2$ incubator, and accordingly the cells were migrated from the upper chamber to the lower chamber. Non-migrated cells remaining on the surface of the upper chamber were eliminated. The cells migrated to the lower chamber were fixed with 3.7% PFA (paraformaldehyde; PBS), followed by staining with 2% crystal violet solution. The crystal violet solution was washed with distilled water, selected region (×200) was photographed, and three randomly selected regions (×200) were measured to calculate the migrated cells. The experiment was performed at least two times to present a representative result. The data was represented as migration cells±standard error.

Figure 5:
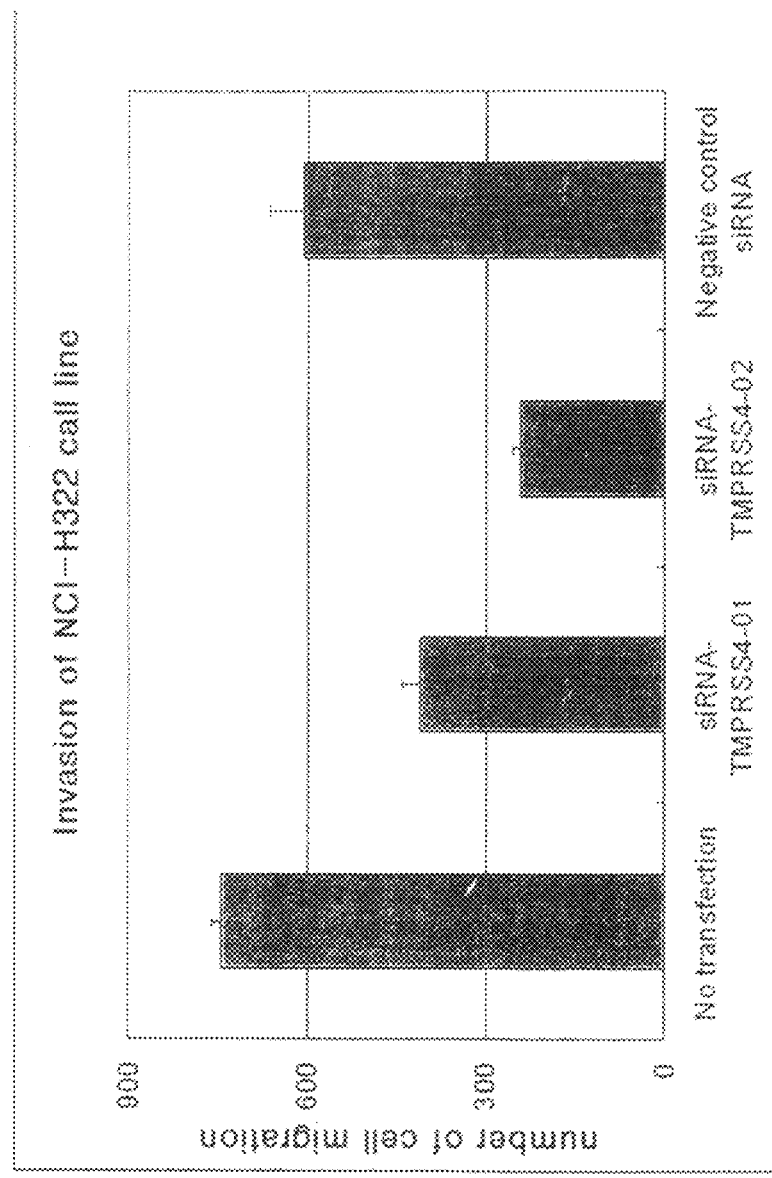
FIG. 5 is a graph illustrating the cell migration after invasion in NCl-H322 cell lines transformed with siRNA.

As a result, cancer cell invasion was clearly inhibited by synthetic siRNA (FIG. 4). In the meantime, cancer cell invasion was hardly inhibited by the negative control siRNA. The cancer cell migration through decomposed matrigel, was 33~60% inhibited in the group transformed with siRNA inhibiting TMPRSS4 expression, compared with the negative control (FIG. 5). siRNA-TMPRSS4-02 exhibited higher inhibitory effect than siRNA-TMPRSS4-01, which seems to be attributed to the difference in time-dependent stability and efficiency among siRNA dimers. Considering that the transformation efficiency was 60%, the observed inhibition of TMPRSS4 expression indicates almost 100% inhibition of cancer cell invasion and metastasis. Therefore, it was confirmed that TMPRSS4 played a critical role in cancer cell invasion and metastasis.

EXAMPLE 3

Invasion by TMPRSS4 Over-Expression (Colon Cancer Cell Line: SW480)

Preparation of TMPRSS4 Over-Expressing Cell Lines

4 µg of pCMV-myc-TMPRSS4 expression vector prepared in Example <2-2> and 10 µl of Lipofectamine™ (Invitrogen, USA) were mixed in 2.5 ml of Opti-MEM, with which SW480, a large intestine cancer cell line, was transformed according to the manufacturer's instruction (Invitrogen, USA). Cells were distributed in a 6 well-plate at the concentration of $3 \times 10^5$ cells/well and 48 hours later the cells were transferred into a selection medium (600 µg/ml G418 medium). G418-resistant clone was separated and cell culture continued for 2 weeks to prepare a TMPRSS4 over-expressing cell line.

<3-2> TMPRSS4 Expression in TMPRSS4 Over-Expressing Cell Lines

RT-PCR was performed with the TMPRSS4 over-expressing cell line prepared in Example <3-1> by the same manner as described in Example <1-2> to investigate TMPRSS4 expression at RNA level. Actin forward primer (5'-GCT CGT CGT CGA CAA CGG CTC-3') represented by SEQ. ID. NO: 15 and actin reverse primer (5'-CAA ACA TGA TCT GGG TCA TCT TCT C-3') represented by SEQ. ID. NO: 16 were used for the RT-PCR. PCR of actin was performed by the same manner and conditions as described in Example <1-2> (PCR of GAPDH). Western blotting was also performed by the same manner as described in Example <2-4> to measure TMPRSS4 expression at protein level.

Figure 6:
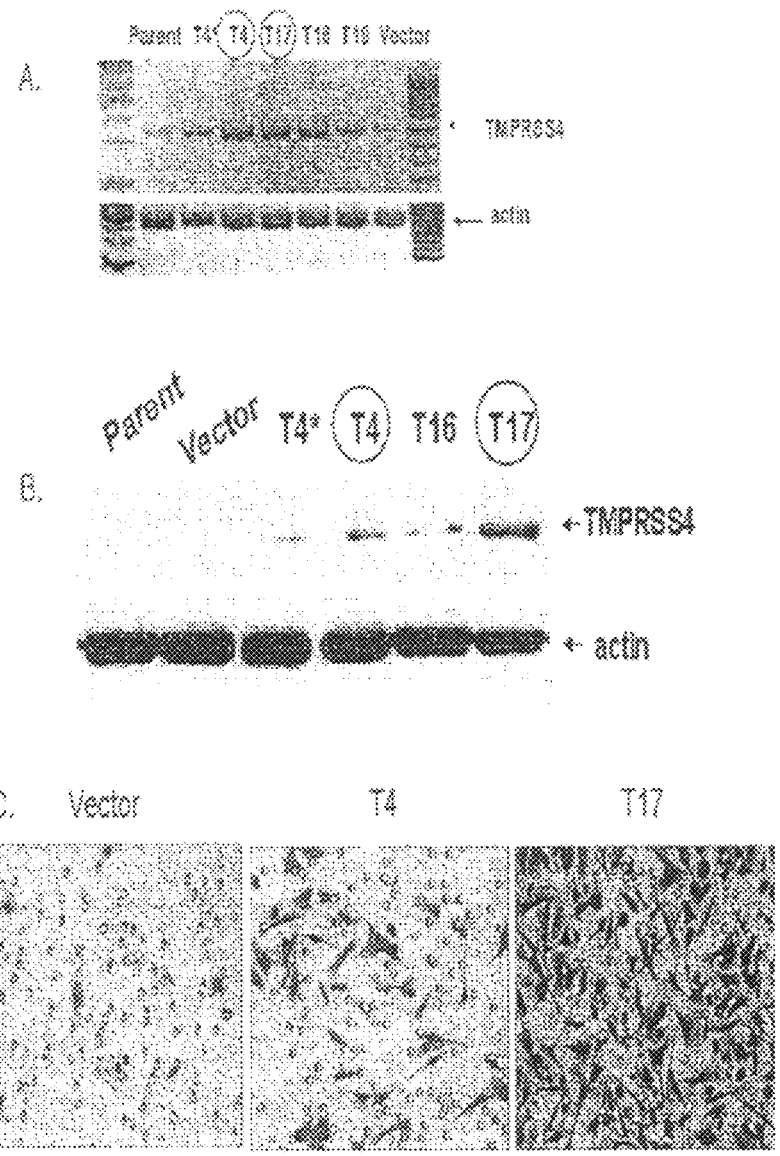
FIG. 6 is a set of photographs illustrating the invasion capacity of TMPRSS4 over-expressing cell lines (SW480).
A: Expression of TMPRSS4 in TMPRSS4 over-expressing cell lines, investigated by RT-PCR;
B: Expression of TMPRSS4 in TMPRSS4 over-expressing cell lines, investigated by Western blotting; and
C: Invasion of TMPRSS4 over-expressing cell lines, investigated by matrigel assay.

As a result, TMPRSS4 expressions in SW480-T4 and SW480-T17 cell lines were three fold higher than that in the negative control cell line transformed with an empty vector (FIG. 6A). The result of Western blotting was consistent with that of RT-PCR, confirming the increase of TMPRSS4 expression (FIG. 6B). In particular, TMPRSS4 expression was comparatively high in SW480-T17 cell line.

<3-3> Invasion Assay with a TMPRSS4 Over-Expressing Cell Line

Invasion assay was performed with SW480-T4 and SW480-T17 cell lines by the same manner as described in Example <2-6>.

As a result, the invasion capacities of SW480-T4 and SW480-T17 cell lines were respectively 5-fold and 14-fold higher than that of the control cell line (FIG. 6C).

EXAMPLE 4

Invasion by TMPRSS4 Over-Expression (Lung Cancer Cell Line: A549)

<4-1> Preparation of TMPRSS4 Over-Expressing Cell Lines

A lung cancer cell line A549 was transformed with pCMV-myc-TMPRSS4 vector constructed in Example <2-2> by the same manner as described in Example <3-1> to prepare a TMPRSS4 over-expressing cell line.

<4-2> TMPRSS4 Expression in TMPRSS4 Over-Expressing Cell Lines

Western blotting was performed with a TMPRSS4 over-expressing A549 cell line prepared in Example <4-1> by the same manner as described in Example <2-4> to investigate TMPRSS4 expression at protein level.

Figure 7:
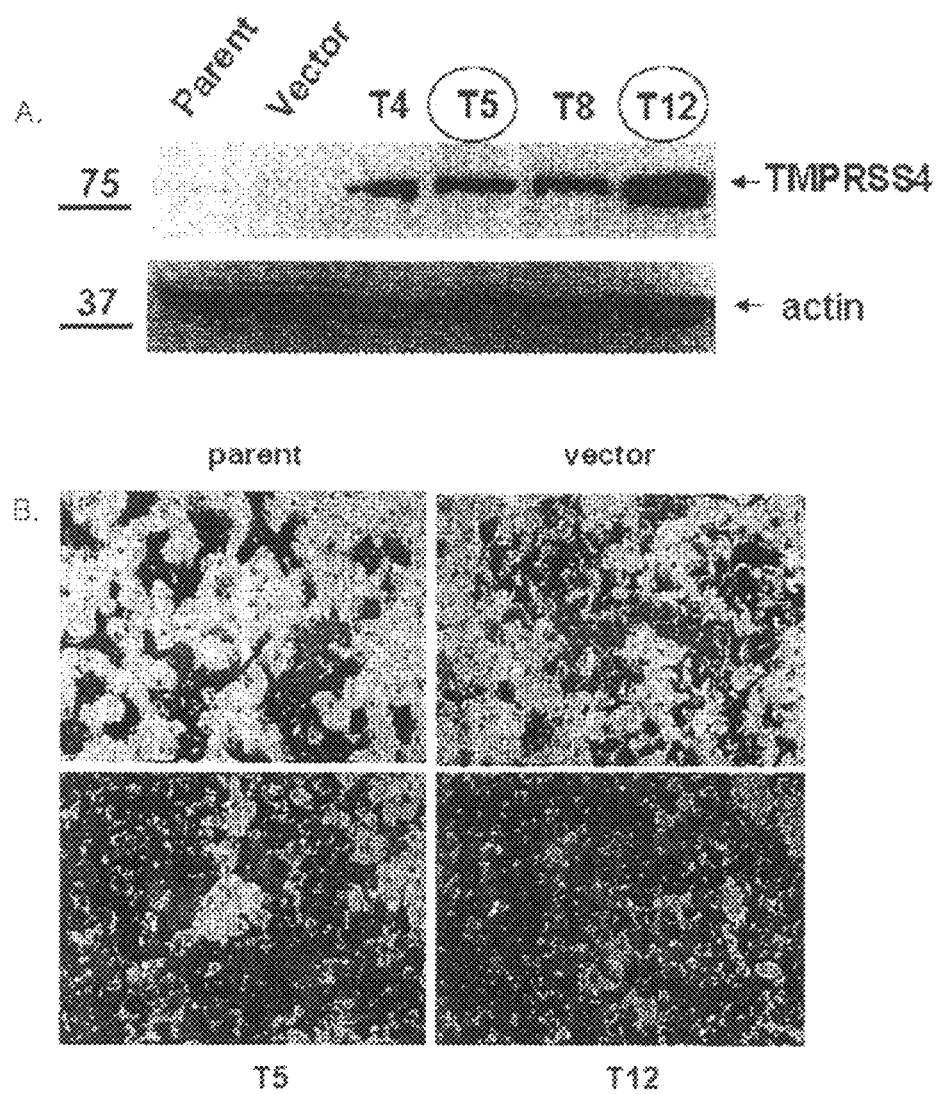
FIG. 7 is a set of photographs illustrating the invasion capacity of TMPRSS4 over-expressing cell lines (A549).

As a result, among A549 cell lines prepared above, A549-T5 and A549-T12 cell lines exhibited significantly increased TMPRSS4 expressions, compared with wild-type A549 or the negative control cell line transformed with an empty vector (FIG. 7A).

<4-3> Invasion Assay with TMPRSS4 Over Expressing Cell Lines

Invasion assay was performed with A549-T5 and A549-T12 cell lines by the same manner as described in Example <2-6>.

As a result, A549-T5 and A549-T12 cell lines exhibited respectively at least three-fold higher invasion capacity than the control cell line (FIG. 7B). From the above result, it was confirmed that TMPRSS4 played a crucial role in cancer cell invasion and metastasis.

EXAMPLE 5

Cell Proliferation Assay

To investigate how the inhibition of TMPRSS4 expression affected cancer cell proliferation, cell growth was observed in a serum-containing or a serum-free medium. Herein, NCI-H322 cell lines transformed with siRNA-TMPRSS4-01 and siRNA-TMPRSS4-02 prepared in Example <2-6> were used. The cells were distributed in a 96 well plate at the concentration of $5 \times 10^3$ cells/well and cultured in a 37° C. 5% $CO_2$ incubator for 24 hours. Cell proliferation was investigated by colorimetric WST assay kit (Takara Bio Inc., Japan). ⅒ volume of WST reagent was added to each well, which stood for 4 hours. Cell growth was measured with a reader at 440 nm. The measurement was performed with three equally prepared samples at the same time and repeated at least twice. 24 hours after cell inoculation, the medium was removed and the cells were washed with PBS. Then, the medium was replaced with a serum-free medium. The cells were cultured for three more days and the cell proliferation was measured by using WST reagent. The data was represented as optical density±standard error.

There were no apparent differences of proliferation between cells when cultured in the serum-containing medium for 72 hours (FIG. 8). However, significant difference in cell growth was observed between cells when cultured in a serum-free medium (FIG. 9). Cancer cells transformed with siRNA were distributed in a 96-well plate. After cells were adhered to the plate, the culture solution was removed and the cells were washed. The washed cells were further cultured in a serum-free medium for 72 hours. Cell proliferation rates in those transformed with siRNA (negative control) were respectively 3.4 fold and 3.1 fold increased, while cell proliferation rates in cell lines transformed with siRNA-TMPRSS4-01 and siRNA-TMPRSS4-02 were respectively 1.9 fold and 2 fold increased (FIG. 9). The above results indicate that TMPRSS4 decreased growth factor-dependency of cancer cell proliferation, which in turn induced abnormal growth of cancer cells.

EXAMPLE 6

Cell Morphology

To investigate the effect of TMPRSS4 over-expression on cell morphology in cancer cells, the present inventors observed TMPRSS4 over-expressing colon cancer cell lines SW480-T4 and SW480-T17 under optical microscope. Cell growth was induced until the population reached 50~60% of the total area of a culture vessel, and observed under Nikon optical microscope (Japan) with 100× magnification.

As a result, cell spreading is clearly increased and lamellipoidia was formed in the edge of cells in SW480-T4 and SW480-T17 cell lines, compared with SW480 and the cell line transformed with an empty vector (FIG. 10).

EXAMPLE 7

Investigation of Intracellular Actin Rearrangement by Immunocytochemistry 1 mm thick glass coverslip was coated with serum at 37° C. for one hour, and then blocked with 3% BSA (bovine serum albumin) at 37° C. for 2 hours. Cells were treated with trypsin and recovered from the cell dish. The recovered cells were transferred onto the coated coverslip, followed by culture in a 37° C. 5% $CO_2$ incubator for 72 hours. The cells were fixed with 3.7% formaldehyde and treated with 0.3% Triton X-100 for 3 minutes. The coverslip was treated with 10% NHS/PBS (10% normal horse serum in PBS; VECTOR Laboratories, Burlingame, USA) and left at room temperature for one hour. After treated with rhodamnine-phalloidin (Molecular Probes, Inc., Eugene, USA), the coverslip was transferred in a humidified chamber and left there at room temperature for one hour. The coverslip was washed with PBS, and mounting solution (VECTOR Laboratories, USA) was loaded on the coverslip. Visualization was performed with a fluorescent microscope (400×, Leica, Germany).

As a result, actin was spread throughout the cells and filament formation was not observed in the negative control cell line transformed with an empty vector. On the other hand, stress fiber formation and intercellular filopodia like structure were observed in TMPRSS4 overexpressing cell lines (FIG. 11). The above effect was more peculiar in SW480-T17 cell line. From the above results, it was confirmed that TMPRSS4 over-expression changed cell morphology by actin cytoskeleton rearrangement and increased cell invasion thereby.

EXAMPLE 8

E-Cadherin Expression

To investigate if TMPRSS4 over-expression was related to the regulation of major factors involved in cell invasion, RT-PCR was performed to measure E-cadherin expression which can induce cell-cell adhesion. Particularly, RT-PCR was performed with SW480-T4 and SW480-T17 by the same manner as described in Example <1-2>, for which E-cadherin forward primer (5'-GGT TAT TCC TCC CAT CAG CT-3') represented by SEQ. ID. NO: 17 and E-cadherin reverse primer (5'-CTT GGC TGA GGA TGG TGT A-3') represented by SEQ. ID. NO: 18 were used. GAPDH was amplified as a control by the same manner as described in Example <1-2>. PCR was performed by the same manner and conditions as described in Example <1-2> (PCR with GAPDH).

As a result, E-cadherin expressions were reduced in SW480-T4 and SW480-T17 cell lines, compared with SW480 cell line or the negative control cell line transformed with an empty vector (FIG. 12). The above result indicates that TMPRSS4 over-expression decreases E-cadherin expression and thereby reduces cell-cell adhesion and induces an epithelial-mesenchymal transition along with actin cytoskeleton rearrangement.

EXAMPLE 9

Degradation of Synthetic TMPRSS4 Substrate

The present inventors investigated degradation capacity of a synthetic TMPRSS4 substrate in order to confirm the possibility of screening for an anticancer agent candidate.

To induce the expression and secretion of the extracellular domain (54~437 amino acids: SEQ. ID. NO: 19) of TMPRSS4 in mammalian cells, the nucleotide sequence (SEQ. ID. NO: 20) corresponding to the extracellular domain of TMPRSS4 (Genebank accession number: AF179224) was inserted into pFLAG-CMV-1 vector (Sigma, USA). The present inventors amplified 54~437 amino acid region of TMPRSS4 by PCR using the primers containing BglII site (SEQ. ID. NO: 21: 5'-TAA GAT CTG GGG TGA CAA TC-3') and SalI site (SEQ. ID. NO: 22: 5'-GTC GAC GTC AGA TTG GTA C-3') respectively. The pFLAG-CMV-1 vector and the PCR product were digested with BglII and SalI, which were inserted into a vector to construct pFLAG-CMV-TMPRSS4 containing the extracellular domain (54~437 amino acids) cDNA of TMPRSS4. At this time, pFLAG-CMV-1 was used as a negative control. 293E cells were transformed with the pFLAG-CMV-TMPRSS4 and pFLAG-CMV-1 by using lipofectamine 2000 (Invitrogen, USA) according to the manufacturer's instruction. 48 hours after transformation, the medium was replaced with a new serum-free medium, followed by further culture. During the culture, conditioned medium was collected for 6 days. Western blotting was performed by using anti-FLAG antibody, resulting in the confirmation of normal secretion of the extracellular domain of TMPRSS4. To investigate protease activity of the extracellular domain of TMPRSS4, the conditioned medium was 40-fold concentrated by using centricon (Millipore, USA) and reacted with 100 µM of the synthetic fluorescent substrate t-butyloxycarbonyl(t-Boc)-Gln-Ala-Arg-7-amido-4-methylcoumarin (Sigma, USA) in Tris buffer (100 mM, Tris pH 8.0) at 25° C. To block the protease activity during the reaction, the serine protease inhibitor AEBSF was added at the concentration of 1 mM. The excitation and emission of the fluorescein generated by hydrolysis of the peptide substrate were measured at 380 nm and 460 nm by using a fluorescence reader Victor 3 (PerkinElmer, USA).

The enzyme activity to the fluorescein peptide substrate t-Boc-Gln-Ala-Arg-AMC, which has been known as a trypsin substrate, was detected in the conditioned medium containing the extracellular domain of TMPRSS4, while only background activity was detected in the negative control (FIG. 13). The enzyme activity was completely inhibited by AEBSF, a serine protease inhibitor. Therefore, it was confirmed that the extracellular domain of TMPRSS4 had trypsin-like serine protease activity.

INDUSTRIAL APPLICABILITY

As explained hereinbefore, the anticancer agent of the present invention contains TMPRSS4 inhibitor as an effective ingredient, which is very effective for the treatment of cancer by functioning to inhibit cancer cell growth and invasion by suppressing TMPRSS4 expression.

[Sequence List Text]

SEQ. ID. NO: 1 is a TMPRSS4 fragment forward primer.
SEQ. ID. NO: 2 is a TMPRSS4 fragment reverse primer.
SEQ. ID. NO: 3 is a TMPRSS4 forward primer.
SEQ. ID. NO: 4 is a TMPRSS4 reverse primer.
SEQ. ID. NO: 5 is a GAPDH forward primer.
SEQ. ID. NO: 6 is a GAPDH reverse primer.
SEQ. ID. NO: 7 is a siRNA-TMPRSS4-01 forward primer.
SEQ. ID. NO: 8 is a siRNA-TMPRSS4-01 reverse primer.
SEQ. ID. NO: 9 is a siRNA-TMPRSS4-02 forward primer.
SEQ. ID. NO: 10 is a siRNA-TMPRSS4-02 reverse primer.
SEQ. ID. NO: 11 is a siRNA-TMPRSS4-03 forward primer.
SEQ. ID. NO: 12 is a siRNA-TMPRSS4-03 reverse primer.

SEQ. ID. NO: 13 is a TMPRSS4 forward primer.
SEQ. ID. NO: 14 is a TMPRSS4 reverse primer.
SEQ. ID. NO: 15 is an actin forward primer.
SEQ. ID. NO: 16 is an actin reverse primer.
SEQ. ID. NO: 17 is an E-cadherin forward primer.
SEQ. ID. NO: 18 is an E-cadherin reverse primer.
SEQ. ID. NO: 19 is an amino acid sequence of extracellular domain (54~437 amino acids) of TMPRSS4.
SEQ. ID. NO: 20 is a nucleotide sequence of extracellular domain of TMPRSS4.
SEQ. ID. NO: 21 is a primer containing BglII site.
SEQ. ID. NO: 22 is a primer containing salI site.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A method for inhibiting metastasis of a cancer cell comprising:
   (i) administering an effective dose of an anticancer agent containing a TMPRSS4 (transmembrane protease, serine 4) inhibitor as an active ingredient; and
   (ii) inhibiting the invasive ability of the cancer cell by inhibiting expression of TMPRSS4 protein;
   wherein
   the TMPRSS4 inhibitor is selected from a group consisting of an antisense nucleotide binding complementarily to TMPRSS4 mRNA, a small interfering RNA (siRNA), and an antibody; and
   the cancer cell is a colon cancer cell or a lung cancer cell.

2. The method of for inhibiting metastasis of a cancer cell according to claim 1, wherein the siRNA has the structure wherein a sense RNA and an antisense RNA form a double stranded RNA together and the sense RNA has the same nucleic acid sequence as the target sequence of 19-25 consecutive nucleotides of TMPRSS4 mRNA.

3. The method for inhibiting metastasis of a cancer cell according to claim 2, wherein the sense RNA comprises a nucleotide sequence of SEQ ID NO: 7, SEQ ID NO: 9 and/or SEQ ID NO: 11.

* * * * *